US008557583B2

(12) United States Patent
Watanabe et al.

(10) Patent No.: US 8,557,583 B2
(45) Date of Patent: Oct. 15, 2013

(54) CELL CULTURE SUPPORT AND MANUFACTURE THEREOF

(75) Inventors: Masanao Watanabe, Tokyo (JP); Kenichi Hagiwara, Tokyo (JP); Teruo Okano, Tokyo (JP); Masayuki Yamato, Tokyo (JP); Tatsuya Shimizu, Tokyo (JP); Yoshikatsu Akiyama, Tokyo (JP); Hiroya Watanabe, Tokyo (JP); Keisuke Ashiba, Tokyo (JP)

(73) Assignees: Dai Nippon Printing Co., Ltd., Tokyo (JP); Tokyo Woman's Medical University, Tokyo (JP); Cellseed Inc., Tokyo (JP)

( * ) Notice: Subject to any disclaimer, the term of this patent is extended or adjusted under 35 U.S.C. 154(b) by 1205 days.

(21) Appl. No.: 12/045,847

(22) Filed: Mar. 11, 2008

(65) Prior Publication Data

US 2008/0227203 A1    Sep. 18, 2008

(30) Foreign Application Priority Data

Mar. 15, 2007    (JP) .................................. 2007-066700
Apr. 20, 2007    (JP) .................................. 2007-111757

(51) Int. Cl.
*C12N 5/00*    (2006.01)
*C12N 5/02*    (2006.01)

(52) U.S. Cl.
USPC .......................................... 435/402; 435/395

(58) Field of Classification Search
None
See application file for complete search history.

(56) References Cited

U.S. PATENT DOCUMENTS

| | | | |
|---|---|---|---|
| 5,271,988 A | 12/1993 | Ikemoto et al. | |
| 5,284,766 A | 2/1994 | Okano et al. | |
| 5,888,650 A * | 3/1999 | Calhoun et al. | 428/354 |
| 5,997,961 A * | 12/1999 | Feng et al. | 427/515 |
| 6,447,897 B1 * | 9/2002 | Liang et al. | 428/336 |
| 2003/0077435 A1 * | 4/2003 | Charkoudian et al. | 428/304.4 |
| 2005/0214935 A1 | 9/2005 | Kuwabara et al. | |
| 2006/0234377 A1 | 10/2006 | Okano et al. | |

FOREIGN PATENT DOCUMENTS

| | | |
|---|---|---|
| EP | 0382214 A1 | 2/1990 |
| EP | 0 382 214 A1 | 8/1990 |
| EP | 1264877 A1 | 12/2002 |
| EP | 1288264 A1 | 3/2003 |
| EP | 1416303 A2 | 10/2003 |
| JP | 2211865 A | 8/1990 |
| JP | 4117466 A | 4/1992 |
| JP | 05-192130 A | 8/1993 |
| JP | 05-244938 A | 9/1993 |
| JP | 5-260957 A | 10/1993 |
| JP | 05-262882 B2 | 10/1993 |
| JP | 06-228319 B2 | 8/1994 |
| JP | 6-104061 B2 | 12/1994 |
| JP | 09-012651 A | 1/1997 |
| JP | 10-248557 A | 9/1998 |
| JP | 11-349643 A | 12/1999 |
| JP | 2001-329183 A | 11/2001 |
| JP | 2002-018270 A | 1/2002 |
| JP | 2003-222704 A | 8/2003 |
| JP | 2003-306434 A | 10/2003 |
| JP | 2004-170935 A | 6/2004 |
| JP | 2004-261533 A | 9/2004 |
| JP | 2005-130838 A | 5/2005 |
| JP | 2005-168494 A | 6/2005 |
| JP | 2006-320304 A | 11/2006 |
| WO | 01/68799 A1 | 9/2001 |

OTHER PUBLICATIONS

Ebara et al., Biomacromolecules, vol. 5, No. 2, 2004, pp. 505-510.*
Ebara et al., Biomacromolecules, vol. 4, No. 2, 2003, pp. 344-349.*
BD Biosciences Labware Document No. LSR00137, May 21, 2001.*
Japanese Office Action dated Apr. 26, 2011, corresponding to Japanese Application No. 2007-111757.
Kai, K. "Polymer Gels Research and Discussion Session", The Society of Polymer Science, Japan, Jan. 27, 2000, pp. 99-100.
Yuji Haraguchi, et al.; "Electrical coupling of cardiomyocyte sheets occurs rapidly via functional gap junction formation"; Biomaterials; 2006; vol. 27; pp. 4765-4774.
Oh Hyeong Kwon, et al.; "Rapid cell sheet detachment from Poly(N-isopropylacrylamide)-grafted porous cell culture membranes"; Journal of Biomed. Mater. Res.; Apr. 2000; vol. 50, No. 1; pp. 82-89.
Louis F. Fieser, et al.; "Reagents for Organic Synthesis"; 1967; John Wiley & Sons, New York, NY; p. 723.
W. Dale Snyder, et al.; "Effect of Molecular Weight on Hydrogen-Deuterium Exchange in a Nonhelical Polyamide"; Journal of the American Chemical Society; Aug. 20, 1975; vol. 97, No. 17; pp. 4999-5003.
Catherine C. Berry, et al.; The influence of microscale topography on fibroblast attachment and motility; Biomaterials; 2004; vol. 25; pp. 5781-5788.
Matthew John Dalby, et al.; "Changes in fibroblast morphology in response to nano-columns produced by colloidal lithography", Biomaterials; 2004; vol. 25; pp. 5415-5422.
Japanese Office Action dated Mar. 27, 2012, issued in Japanese Application No. 2007-066700.
Year 2003 New Technology Research Project for Achieving Objects Summary of Research Results Report.

* cited by examiner

*Primary Examiner* — Chris R Tate
*Assistant Examiner* — Douglas F White
(74) *Attorney, Agent, or Firm* — Sughrue Mion, PLLC

(57) ABSTRACT

An object of the present invention is to provide a cell culture support making the detachment of a cell sheet easy as well as enabling the formation of a uniform cell sheet. The present invention relates to a method for manufacturing a cell culture support having a temperature responsive polymer immobilized onto the surface thereof via covalent bonding, the method including a coating step in which a composition including a monomer that can form the polymer by polymerization by radiation irradiation, an organic solvent and, in some cases, a prepolymer formed by polymerization of the monomer is coated onto the substrate having a surface containing a material which can be covalently bonded to the temperature responsive polymer by radiation irradiation to form a film on the surface of the substrate, a radiation irradiation step in which a polymerization reaction and a binding reaction between the substrate surface and the temperature responsive polymer are allowed to proceed by irradiating radiation to the film, and a drying step to dry the film.

7 Claims, No Drawings

CELL CULTURE SUPPORT AND MANUFACTURE THEREOF

BACKGROUND OF THE INVENTION

1. Field of the Invention

The present invention relates to a cell culture support for stable mass production of cell sheets.

2. Background Art

A cell sheet is a sheet-form cell aggregate, in which cells are connected via intercellular junction at least in a single layer. Cell sheets are used in regenerative medicine and the like. A cell sheet can be obtained by culturing cells on a cell culture support such as a Petri dish. However, a cell sheet formed on a cell culture support is tightly adhered to the surface of the cell culture support via adhesion molecules and the like. Therefore, it is not easy to detach a cell sheet from a cell culture support rapidly without breaking the cell-to-cell junctions.

Under the circumstances, studies have been made on methods for efficiently detaching a cell sheet from a cell culture support. The detaching methods can be classified into two groups. In the first method, the interaction between a cell culture support and cells is weakened by an enzymatic reaction. In the second method, a cell culture support whose cell adhesive ability is weak or can vary is used.

To explain more specifically, in the first method, enzymes such as protease (proteolysis enzyme) and collagenase (collagenolytic enzyme) are used to degrade proteins constituting intercellular adhesion molecules (involved in tight junction, adherens junction, desmosome junction, gap junction and hemi desmosome junction), collagen matrix surrounding a culture and the extracellular matrix (ECM) formed between cells and a cell culture support. In this method, not only the interaction between cells and the surface of a cell culture support but also cell-cell junctions are weakened. The method has long been used in the field of cell culture. Since the binding substances which are degraded by the method are those produced in cells, tissues and organs to be cultured, they can be regenerated in certain conditions and period of time after a cell sheet is detached.

Nevertheless, the first method has problems. It requires a long time to regenerate the binding substances. Moreover, the cell sheet formed by the method is more or less damaged. Thus, the method is not suitable as a method for manufacturing a cell sheet for use in regenerative medicine.

Under these circumstances, the second method, which uses a cell culture support whose cell adhesive ability is weak or can vary, has been newly developed.

Examples of such cell culture support whose cell adhesive ability is weak include the supports disclosed in Patent Document 1 and Patent Document 2. These documents disclose technique with which cells are cultured on a cell culture support having fine pillars called nanopillars on the surface. With this technology, the cell culture support and a culture material are in contact with each other only at an extremely small area. Therefore, it is believed easy to detach and recover a cell sheet with little damage to the cell sheet.

Nevertheless, as is described in Non-Patent Documents 1 and 2, cell adhesion and the behavior of cells adhered differ depending on whether the cells are adhered to a flat surface or an irregular surface. Culturing on the nanopillars has such problems that adhesion of cells and extension of a cell sheet are delayed, and pseudopoium is formed from a cell surface. Moreover, cells enter the depressions when the depressions of the cell culture support have a width of 20 μm or more.

Examples of a cell culture support whose cell adhesion ability can vary include a cell culture support having a coating of a temperature responsive polymer on the cell proliferation surface thereof (Patent Document 3). A temperature responsive polymer is most preferably used for the purpose of altering cell adhesion ability. Besides this, however, a pH responsive polymer and an ion responsive polymer can also be used. Patent Documents 1 and 2 describe that a temperature responsive polymer is used in combination with culture using nanopillars. The use of a temperature responsive polymer in cell culture is also mentioned in Patent Document 4.

As a method for manufacturing a temperature responsive polymer layer, Patent Document 3 describes a graft polymerization method, in which a polymerization reaction of monomers by electron beam irradiation and a reaction to immobilize (graft) a temperature responsive polymer to a substrate surface by covalently binding at least one end of the temperature responsive polymer to the molecule constituting the substrate are performed. Nevertheless, as is described in Patent Document 4, a temperature responsive polymer layer formed by the graft polymerization method had a problem that it exhibited temperature responsiveness only when a ratio of materials used and conditions for electron beam irradiation are constant.

Patent Document 4 discloses that the amount of a solvent is determined to lower the amount of the residual solvent in a material monomer/solvent mixture to be coated onto a substrate surface before electron beam irradiation. However, in the methods described in Examples and Comparative Examples in Patent Document 4, complicated process control was required for ensuring reproducibility in the amount of the residual solvent, such as drying under natural condition in a constant temperature and humidity chamber, drying under a nitrogen gas stream, vacuum drying and drying by heating within the range not affecting the polymerization of residual monomers. In addition, in Examples and Comparative Examples in Patent Document 4, a solvent whose boiling temperature is 120° C. or lower is used as a solvent to dissolve the coating material for the purpose of improving the polymerization efficiency by electron beam energy. When a composition in which a monomer material is dissolved into such solvent is deposited on the dish to coat, there was a problem that the monomer tended to crystallize. Existence of microcrystals was confirmed by microscopic observation even when no crystal is visible to the naked eye.

The present inventors conducted studies and thus found a problem that a sufficient amount of a temperature responsive polymer is not coated, since polymerization is inhibited in crystal regions when the film with monomer crystals is irradiated with an electron beam. To use the temperature responsive polymer, only the grafted polymers are exposed by washing away the excess free polymers after the graft polymerization by radiation. It is assumed to be effective to reduce the amount of the material used for coating to reduce irregularity of the coated surface and shorten the washing time. However, reducing the amount of the material used for coating was problematic because the reduction would result in promoting crystallization.

The present inventors possess many technologies in the field of printed phase technology with the use of materials for electron beam, such as anti-fog film and coated plywood board. The present inventors have found that a film to which a polymerizable oligomer and a prepolymer are added has excellent decorative coating properties for printing, coating and adhesive hardening by electron beam irradiation (Patent Document 5).

When a temperature responsive polymer is grafted on a substrate surface with the use of radiation, the conditions for each radiation are determined to obtain a uniform distribution of the polymer to be grafted on the substrate. Nevertheless, there were cases where the detachment of the cell sheet did not proceed smoothly depending on the material constituting the substrate, even though the polymer was successfully immobilized onto the substrate surface and a hydrophilic/hydrophobic transition was induced by the aforementioned polymer.

On the other hand, Patent Document 15 discloses a method of multilayered culture for epithelial type cells, in which, when epithelial type cells are cultured on a porous membrane for a cell culture insert, both of the upper layer and the lower layer divided by the porous membrane are filled with a culture medium, and the culture medium is constantly supplied from the lower layer to the cells through the porous membrane while the cells are cultured. In addition, Patent Document 15 also discloses that a temperature responsive polymer is deposited on the aforementioned porous membrane. The cell culture insert disclosed in Patent Document 15 enables a cell culture on a permeable porous membrane, in which the components of the liquid culture medium are diffused to both luminal and basal sides of the cells, similarly to the in vivo process, in an attempt to achieve an in vitro cell culture which is physiologically similar to the in vivo environment. By using the cell culture insert, it is made possible to perform a three-dimensional culture, co-culture for 2 kinds of cells, cell migration/infiltration assay using cells passing through a porous membrane, drug penetration assay using a drug passing through a porous membrane and the like. The cell sheet being cultured by a release culture with the use of a feeder cell and cell growth factor on the undersurface of a cell culture insert can provide more multilayered cells and, in addition, more consistent vertical orientation than the ones being cultured without a feeder or by directly filling a Petri dish with a culture medium containing a cell growth factor. For example, corneal epithelial cells form a multilayer with their basal side down, and mucosal cells are oriented to have their microvilli up.

Patent Document 17 describes that in relation to cardiac muscle treatment using a cell sheet, the cardiac muscle cultured on a substrate to which a temperature responsive polymer is disposed is detached as a cell sheet, and can be used as a transplantable cardiac muscle cell sheet for improving the cardiac function and suppressing cardiac deformation.

Non-Patent Document 6 describes that the cardiac muscle cell sheet manufactured by this method exhibits autonomous pulsating and that when the cell sheets are bilayered, they are adhered with each other with the ECM without sutures, and the bilayered sheet exhibits a synchronously pulsating over a short period of time.

However, it is known that the autonomously pulsating cell sheet manufactured by this method has a random pulse orientation and, thus, if used for treating cardiac muscle, the cell sheet adjusts its orientation to that of a heart receiving transplantation of the cell sheet, which has oriented pulsating, when transplanted to the heart, and the cardiac muscle cell sheet itself adjusts its orientation to the expansion and contraction orientation by repeating expansion and contraction by adding an external force in the culture medium.

However, problems occurred when a cell sheet detached from a substrate was maintained in a culture medium until the cardiac muscle cell sheet itself acquired its own expansion and contraction orientation. The ECM of the sheet was eliminated (digested), and rapid adhesion at the time of transplantation and synchronization of expansion and contraction of the pulse were difficult to take place.

Patent Document 1: JP Patent Publication (Kokai) No. 2004-170935 A
Patent Document 2: JP Patent Publication (Kokai) No. 2005-168494 A
Patent Document 3: JP Patent Publication (Kokoku) No. 6-104061 A (1994)
Patent Document 4: JP Patent Publication (Kokai) No. 5-192130 A (1993)
Patent Document 5: JP Patent No. 2856862
Patent Document 6: JP Patent No. 312660
Patent Document 7: JP Patent No. 3491917
Patent Document 8: JP Patent Publication (Kokai) No. 9-12651 A (1997)
Patent Document 9: JP Patent Publication (Kokai) No. 10-248557 A (1998)
Patent Document 10: JP Patent Publication (Kokai) No. 11-349643 A (1999)
Patent Document 11: JP Patent Publication (Kokai) No. 2001-329183 A
Patent Document 12: JP Patent Publication (Kokai) No. 2002-18270 A
Patent Document 13: JP Patent Publication (Kokai) No. 5-244938 A (1993)
Patent Document 14: International Patent Application No. WO 01/068799
Patent Document 15: JP Patent Publication (Kokai) No. 2005-130838 A
Patent Document 16: JP Patent Publication (Kokai) No. 2006-320304 A
Patent Document 17: JP Patent Publication (Kokai) No. 2003-306434 A
Non-Patent Document 1: M. J. Dalby et al., Biomaterials, 25, 5415-5422 (2004)
Non-Patent Document 2: C. C. Berry et al., Biomaterials, 25, 5781-5788 (2004)
Non-Patent Document 3: W. D. Snyder et al., J. Am. Chem. Soc., 97, 4999 (1967)
Non-Patent Document 4: L. F. Fieser et al., "Reagents for Organic Synthesis," John Wiley & Sons, New York, N.Y., 1967
Non-Patent Document 5: O. H. Kwon, J. Biomed. Mater. Res., April (2000); 50 (1): 82-9
Non-Patent Document 6: Y. Haraguchi et al., Biomaterials, 27, 4765-4774 (2006)

SUMMARY OF THE INVENTION

1. Problems to be Solved by the First Invention

As described above, in the conventional method for manufacturing a cell culture support to manufacture a cell sheet, a monomer/solvent mixture having a small amount of a residual solvent needed to be coated onto the substrate surface and radiation irradiation was required in order to form a uniform temperature responsive graft polymer layer on the substrate surface. Nevertheless, in the film formed by coating the substrate with a composition including a material monomer having a small amount of a solvent, microcrystals of the monomer are likely to be formed. As a result, the film becomes a sea island form composed of monomer microcrystals and a monomer solution. When a polymerization reaction and a grafting reaction of the polymer are conducted by irradiating an electron beam to this film, the island shaped crystal region has a weak cell detachment function owning to its slow grafting, and the sea shaped monomer solution region has a strong cell detachment function owning to its fast grafting. The polymer-coated cell culture support obtained by this method had a problem that the cells could not be uniformly adhered or proliferate thereon. In addition, it had a problem that the cells were not likely to uniformly reach confluence on the cell culture support. Moreover, when confluent cells were to be obtained as a cell sheet, it had problems such as that the sheet was not detached, the detachment of the sheet was delayed, the sheet was damaged, deformation occurred in the sheet even if it was detached without being damaged, and damages were caused to the cells.

In addition, problems occurred when a solvent whose boiling temperature was high was used to prepare a material monomer/solvent mixture for coating the substrate in order to avoid crystallization of the monomer. The radiation efficiency was reduced, and a necessary amount of the graft polymer could not be obtained. Moreover, increasing the amount of the material monomer/solvent mixture for coating had problems. In addition to requiring a longer time for washing, irregularity was created on the surface, as was with a large amount of the residual solvent, owning to the difficulty in uniform drying and radiation irradiation, which resulted in failure to obtain a flat and smooth surface for use as a culture substrate. There were problems associated with the phenomena such as a hydrophilic/hydrophobic transition due to temperature change and the detachment of a cell sheet. For example, the detachment occurred location-dependently, and a dynamic overall detachment was prevented because it had the sea portion of the polymer, being partly resistant to change.

The object of the first invention is to provide a cell culture support which solves the above mentioned problems.

2. Problems to be Solved by the Second Invention

The technology of grafting an environment responsive polymer such as a temperature responsive polymer on a substrate surface of a cell culture support has many advantages. Nevertheless, as far as the material constituting the substrate concerned, there is still room for improvement.

When a temperature responsive polymer is grafted on a substrate surface with the use of radiation, the conditions for each radiation are determined to obtain a uniform distribution of the polymer to be grafted on the substrate. Nevertheless, there were cases where the detachment of the cell sheet did not proceed smoothly depending on the material constituting the substrate, even though the polymer was successfully immobilized onto the substrate surface and a hydrophilic/hydrophobic transition was induced by the aforementioned polymer.

In relation to the material constituting the substrate, Patent Documents 3 and 4 describe that not only the materials which are generally used for cell culture such as glass, modified glass, polystyrene and polymethylmethacrylate but also materials which are generally shapable such as polymer compounds other than those above, ceramics, metals can all be used as the material of the support to which coating is performed. The documents describe that the shape is not limited to a Petri dish and it can be provided as plates, fibers, (porous) particles and shapes of containers (such as flasks) which are generally used for cell culture and the like. Nevertheless, the fact is that, in relation to general-purpose substrates other than polystyrene used for a Petri dish, research reports and conference presentations have been made only for a substrate treated with a silane coupling agent on a slide glass surface or a glass surface or a porous polyethylene terephthalate (PET) film described in Non-Patent Document 5 and the like.

Although it is known that the surface of a temperature responsive graft polymer can be formed on a glass surface by radiation, the surface of the temperature responsive graft polymer formed by this method had a problem of not exhibiting significant cell sheet detachment in comparison with that of a polystyrene Petri dish. In addition, it is known that, when a temperature responsive polymer is grafted on a substrate surface treated with a silane coupling agent, significant cell sheet detachment owning to temperature responsiveness cannot be achieved, and cell adhesion to the substrate surface deteriorates, resulting in failure of forming a favorable cell sheet in comparison with the case where a temperature responsive polymer is grafted on a polystyrene surface.

It has been confirmed that temperature responsiveness is not exhibited depending on conditions of manufacture when re-examining Non-Patent Document 5 with the use of a PET microporous film. To manufacture a temperature responsive cell sheet support effective for use as a cell culture insert, indispensable is the technology to bind a temperature responsive polymer on the surface of a microporous film so that the polymer can function. So far, however, such technology has not been provided.

In addition, it was confirmed that, when a cell sheet was cultured with the use of a temperature responsive graft polymer formed on a PET substrate, which is a general-purpose plastic, in a preliminary experiment of the present invention, the aforementioned substrate did not have a cell sheet detachment function. Moreover, when polycarbonate was used as the substrate, it showed a weaker hydrophilic/hydrophobic transition and weaker cell sheet detachment in comparison with the case where polystyrene was used as the substrate.

Patent Document 17 describes "a transplantable mammalian cardiac muscle cell sheet" and "a cardiac muscle cell sheet to be used for cardiac muscle regenerative treatment." These technologies were observed in small animals such as rats, however. With regards to "transplantation" and "regenerative treatment" in large animals such as humans, cows and pigs among mammals, the cardiac muscle cell sheet which is multilayered into a bilayer as described in Examples had many problems in constructing a cardiac muscle tissue having a contractile and relaxant function to send out blood throughout the body.

One of the problems is that the central portion of a cardiac muscle cell sheet which has 4 layers or more undergoes necrosis due to oxygen deficiency, although "transplantation" and "regenerative treatment" in large animals require a multilayered cardiac muscle cell sheet which is multilayered into 5 layers and 6 layers or more, having a sufficient strength and contractile and relaxant function. The inventors of Patent Document 17 and the authors of Non-Patent Document 6 have succeeded in preventing necrosis due to multilayering of a cell sheet by laminating two 3-layered cell sheets each other after transplanting a 3-layered cell sheet and constructing a network of capillaries.

Another problem is that the cardiac muscle cell sheet to be detached does not have a pulse orientation although the pulse orientation of a sheet-like cardiac muscle tissue, wherein cells are first cultured to confluence with the use of a culture dish coated with poly-N-isopropylacrylamide, which is a temperature responsive polymer, and subsequently the sheet-like cardiac muscle tissue is detached after low-temperature treatment, must conform to the cardiac muscle cell tissue receiving "transplantation" and "regenerative treatment." To adjust the expansion and contraction orientation of the cell sheet, the cell sheet is transplanted close to a muscle tissue and the like with a fixed expansion and contraction orientation or is externally and passively trained for expansion and contraction movements in a cell culture medium as was used for preventing necrosis.

To solve either one of these problems, a cardiac muscle cell sheet manufactured is transplanted to a mammal or undergoes muscle training in a cell culture medium for a predetermined period of time. In doing so, the extracellular matrix (ECM) formed in the detached surface of a sheet-like cardiac muscle cell tissue to be detached, wherein cells are first cultured to confluence with the use of a culture dish coated with poly-N-isopropylacrylamide, which is a temperature responsive polymer, and subsequently the sheet-like cardiac muscle tissue is detached after low-temperature treatment, is involved in rapid cell-to-cell adhesion and engraftment to a host cardiac muscle as well as formation of an electric coupling (gap junction). The ECM disappears as it comes in direct contact with transplantation and a culture medium. Therefore, temperature responsiveness needs to be given to the surface of a transplantable material having flexibility, retractility as well as high gas permeability.

The object of the second invention is to provide a cell culture support which solves the above mentioned problems.

The present application includes the following inventions. Among the following inventions, the invention described in (1) and an invention referring to (1) may be termed "the first invention," and the invention described in (16) and an invention referring to (16) may be termed "the second invention" respectively.

(1) A method for manufacturing a cell culture support having at least one polymer selected from the group consisting of a temperature responsive polymer, a pH responsive polymer and an ion responsive polymer immobilized onto the surface thereof via covalent bonding, comprising a coating step in which a composition comprising a monomer that can form the polymer by polymerization by radiation irradiation, an oligomer or prepolymer formed by polymerization of the monomer, and an organic solvent is coated onto the substrate having a surface containing a material which can be covalently bonded to the polymer by radiation irradiation to form a film on the surface of the substrate, a radiation irradiation step in which a polymerization reaction and a binding reaction between the substrate surface and the polymer are allowed to proceed by irradiating radiation to the film, and a drying step to dry the film.

(2) The method according to above (1), wherein the aforementioned polymer is a temperature responsive polymer.

(3) The method according to above (2), wherein the temperature responsive polymer is either an acrylic polymer or a methacrylic polymer.

(4) The method according to above (3), wherein the acrylic polymer is poly-N-isopropylacrylamide.

(5) The method according to any one of the above (1) to (4), wherein the aforementioned composition has a viscosity in the range of $5 \times 10^{-3}$ Pa·s to 10 Pa·s.

(6) The method according to any one of the above (1) to (5), wherein a molecular weight of the aforementioned oligomer or prepolymer is 3000 or more.

(7) The method according to any one of the above (1) to (6), wherein a weight ratio of the aforementioned monomer and the aforementioned oligomer or prepolymer is in the range of 500:1 to 1:20.

(8) The method according to any one of the above (1) to (7), wherein the radiation irradiation step is conducted in a single shot irradiation of radiation.

(9) The method according to any one of the above (1) to (8), wherein the radiation is either γ rays or an electron beam.

(10) The method according to any one of the above (1) to (9), wherein the radiation is an electron beam whose radiation dosage is in the range of 5 Mrad to 50 Mrad, or γ rays whose radiation dosage is in the range of 0.5 Mrad to 5 Mrad.

(11) The method according to any one of the above (1) to (10), wherein the drying step is conducted prior to the radiation irradiation step.

(12) The method according to any one of the above (1) to (11), wherein the shape of the substrate is film-shape.

(13) The method according to above (1), wherein the substrate comprises at least one material selected from the group consisting of polystyrene, low-density polyethylene, medium-density polyethylene, high-density polyethylene, polyurethane, an acrylic resin, polyamide, polycarbonate, a natural rubber having covalent bonds, synthetic rubber having covalent bonds, a silicon rubber containing polysilicon, microporous polycarbonate, polyethylene terephthalate whose surface is treated with an adhesion-improving treatment, a synthetic resin whose surface is processed with either corona treatment or plasma treatment, and a synthetic resin whose surface is coated with an acrylic resin.

(14) The method according to above (13), wherein the synthetic resin is at least one material selected from the group consisting of nylon, low-density polyethylene, medium-density polyethylene, polypropylene, polyethylene terephthalate, polycarbonate and polystyrene.

(15) The method according to above (13), wherein the synthetic resin whose surface is processed with either corona treatment or plasma treatment is at least one selected from the group consisting of microporous nylon, microporous polyethylene, microporous polypropylene, microporous polyethylene terephthalate, and microporous polycarbonate, whose surface is processed with either corona treatment or plasma treatment.

(16) A method for manufacturing a cell culture support comprising a substrate having at least one environment responsive polymer selected from the group consisting of a temperature responsive polymer, a pH responsive polymer and an ion responsive polymer immobilized onto the surface thereof via covalent bonding, comprising a coating step in which a composition containing a monomer that can form the environment responsive polymer by polymerization by radiation irradiation and an organic solvent is coated onto a substrate having a surface which can be covalently bonded to the environment responsive polymer by radiation irradiation to form a film on the surface of the substrate, a radiation irradiation step in which a polymerization reaction to form the environment responsive polymer and a binding reaction between the environment responsive polymer and the substrate surface are allowed to proceed by irradiating radiation to the film, and a drying step to dry the film, wherein the substrate comprises at least one material selected from the group consisting of polyethylene terephthalate whose surface is treated with an adhesion-improving treatment, a synthetic resin whose surface is processed with either corona treatment or plasma treatment, and a synthetic resin whose surface is coated with an acrylic resin, a natural rubber having covalent bonds, a synthetic rubber having covalent bonds, a silicon rubber containing polysilicon and microporous polycarbonate.

(17) The method according to above (16), wherein the synthetic resin is at least one selected from the group consisting of nylon, low-density polyethylene, medium-density polyethylene, polypropylene, polyethylene terephthalate, polycarbonate and polystyrene.

(18) The method according to above (16), wherein the synthetic resin whose surface is processed with either corona treatment or plasma treatment is at least one selected from the group consisting of microporous nylon, microporous polyethylene, microporous polypropylene, microporous polyethylene terephthalate, and microporous polycarbonate, whose surface is processed with either corona treatment or plasma treatment.

(19) A cell culture support manufactured by the method according to above (1), wherein at least one polymer selected from the group consisting of a temperature responsive polymer, a pH responsive polymer and an ion responsive polymer is immobilized onto the surface thereof via covalent bonding. The thickness of the aforementioned polymer layer immobilized onto the surface of the cell culture support is preferably in the range of 0.001 to 10 μm when dried.

(20) A cell culture support manufactured by the method according to above (16), wherein at least one environment responsive polymer selected from the group consisting of a temperature responsive polymer, a pH responsive polymer and an ion responsive polymer is immobilized onto the surface thereof via covalent bonding, and wherein the support comprises a substrate comprising at least one material selected from the group consisting of polyethylene terephthalate whose surface is treated with an adhesion-improving treatment, a synthetic resin whose surface is processed with either corona treatment or plasma treatment, a synthetic resin whose surface is coated with an acrylic resin, a natural rubber having covalent bonds, a synthetic rubber having covalent bonds, a silicon rubber containing polysilicon and microporous polycarbonate. The thickness of the aforementioned environment responsive polymer layer immobilized onto the surface of the aforementioned substrate is preferably in the range of 0.001 to 10 μm when dried.

(21) A method for manufacturing a cell sheet, comprising a step of culturing cells on the cell culture support according to above (19).

(22) A method for manufacturing a cell sheet, comprising a step of culturing cells on the cell culture support according to above (20).

(23) A cell sheet manufactured by the method according to above (21).

(24) A cell sheet manufactured by the method according to above (22).

1. Advantages of the First Invention

With the cell culture support according to the present invention, various polymers can be grafted on all over the substrate because precipitation and crystallization of monomers do not occur even when the amount of a residual solvent is lowered before radiation irradiation.

With the cell culture support according to the present invention, thin-film coating can be conducted and the washing time after radiation irradiation can be reduced because precipitation and crystallization of monomers do not occur even when the amount of a residual solvent is lowered before radiation irradiation.

When a cell sheet is manufactured with the use of the cell culture support according to the present invention, cell adhesion and cell proliferation are facilitated, cells can reach confluence (a state in which adjacent cells are adhered to one another without a gap, aggregated and populated) or a state close to confluence all over the substrate surface in a shorter period of time, and the culture time prior to cell sheet detachment can be reduced because the cell sheet does not contain unnecessary polymers.

When a cell sheet is manufactured with the use of the cell culture support according to the present invention, cells reach confluence (or almost confluent) without exhibiting partial delay in culturing and, thus, the cell sheet being detached has neither discontinuity nor damage. As a result, a uniform cell sheet can be obtained.

When the cell culture support according to the present invention contains a temperature responsive graft polymer layer on the surface thereof, wettability of the surface varies in accordance with temperature, and the support exhibits reversibly favorable cell adhesion and detachability.

A cell sheet manufactured with the use of the cell culture support according to the present invention is suitable for use in regenerative medicine and the like because the adhesive factors on the surface of the cell sheet are not impaired.

2. Advantages of the Second Invention

According to the method for manufacturing a cell culture support according to the present invention, an environment responsive polymer can be directly grafted on the substrate surface without the aid of a silane coupling agent. Therefore, cell adhesion occurs uniformly on the substrate during culture, cells reach a state of uniform confluence, and a less-damaged cell sheet can be obtained.

According to the method for manufacturing a cell culture support according to the present invention, an environment responsive polymer can effectively be grafted on a microporous synthetic resin film without impairing medium permeability of the aforementioned film. The cell culture support obtained by this method can be used for an insert culture.

According to the method for manufacturing a cell culture support according to the present invention, an environment responsive polymer can be grafted on the surface of a rubber, plastic and the like, which are transplantable and expandable and contractable for cell orientation.

When the cell culture support manufactured by the method according to the present invention contains a temperature responsive graft polymer layer on the surface thereof, wettability of the surface varies in accordance with temperature, and the support exhibits reversibly favorable cell adhesion and detachability. In addition, the ECM is maintained both in vivo and in vitro (such as in a culture medium) after detaching a cell sheet by lowering the temperature. Therefore, the cell sheets detached can be adhered to one another in 30 minutes or less without sutures including gap junctions. As a result, a cell sheet with many of various cell binding functions preserved can be obtained.

In addition, according to the method of the present invention, an environment responsive polymer can be grafted on the surface of a transplantable material having flexibility, retractility as well as high gas permeability. The problem that the ECM of a cell sheet disappears in half a day or more as it comes in direct contact with transplantation within a living organism and a culture medium can be avoided.

A cell sheet manufactured with the use of the cell culture support according to the present invention is suitable for use in regenerative medicine and the like because the adhesive factors on the surface of the cell sheet are not impaired.

DETAILED DESCRIPTION OF THE PREFERRED EMBODIMENTS

The present invention will now be described more specifically hereinafter. The following description fits into both the first and second inventions, unless otherwise specified.

[Environment Responsive Polymer]

The present invention relates to a method for manufacturing a cell culture support equipped with a substrate having at least one environment responsive polymer selected from the group consisting of a temperature responsive polymer, a pH responsive polymer and an ion responsive polymer immobilized (namely, grafted) to the surface thereof via covalent bonding.

Preferred environment responsive polymers are, but not limited to, temperature responsive polymers.

A temperature responsive polymer preferably used in the present invention exhibits hydrophobicity at a cell culture temperature (generally in the range of 37° C.), and hydrophilicity at the temperature at which the cell sheet being cultured is recovered. In addition, the temperature at which the temperature responsive polymer shifts from hydrophobic to hydrophilic (critical dissolution temperature relative to water (T)) is preferably lower than the cell culture temperature in terms of the easiness in cell sheet recovery after culture, but is not specifically limited. By containing such a temperature responsive polymer component, cell scaffold (cell adhesion surface) is sufficiently secured during cell culture and, thus, cell culture can be conducted efficiently. On the other hand, when the cell sheet is recovered after culture, the cell sheet being cultured is detached from the cell culture substrate by altering its hydrophobic portions to hydrophilic, which makes it possible to further facilitate cell sheet recovery. Particularly preferred are temperature responsive polymers which exhibit hydrophilicity at a temperature lower than a predetermined critical dissolution temperature, and hydrophobicity at a temperature above or equal to the same temperature. The critical dissolution temperature for such temperature responsive polymers is specifically termed a lower critical dissolution temperature.

More specifically, the temperature responsive polymer which can be preferably used in the present invention is a polymer whose lower critical dissolution temperature T is in the range of 0 to 80° C., and more preferably 0 to 50° C. It is not preferable for T to exceed 80° C. because there is a possibility that cells are killed. In addition, if T is lower than 0° C., the rate of cell proliferation is significantly reduced, or cells are killed in general. This is thus not preferred. Examples of such preferred polymers include acrylic polymers or methacrylic polymers. Examples of preferred polymers are also described in Patent Document 3. More specifically, examples of suitable polymers include poly-N-isopropylacrylamide (T=32° C.), poly-N-n-propylacrylamide (T=21° C.), poly-N-n-propylmetacrylamide (T=32° C.), poly-N-ethoxyethylacrylamide (T=approximately 35° C.), poly-N-tetrahydrofurfurylacrylamide (T=approximately 28° C.), poly-N-tetrahydrofurfurylmetacrylamide (T=approximately 35° C.) and poly-N,N-diethylacrylamide (T=32° C.). Examples of other polymers include poly-N-ethylacrylamide, poly-N-isopropylmetacrylamide, poly-N-cyclopropylacrylamide, poly-N-cyclopropylmetacrylamide, poly-N-acryloylpyrrolidine, poly-N-acryloylpiperidine, polymethylvinyl ether, alkyl substituted cellulose derivatives such as methylcellulose, ethylcellulose, and hydroxypropyl cellulose, polyalkylene oxide block copolymers as exemplified by a block copolymer of polypolypropylene oxide and polyethylene oxide and the like, and polyalkylene oxide block copolymers.

Examples of monomers to form these polymers include monomers which form homopolymers having T in the range of 0 to 80° C., and monomers which can polymerize by radiation irradiation. Examples of monomers include (meth) acrylamide compounds, N-(or N,N-di)alkyl substituted (meth)acrylamide derivatives, (meth)acrylamide derivatives having a cyclic group and vinyl ether derivatives. One or more of these may be used. When one monomer is used, polymers to be formed on the substrate are homopolymers. When a plurality of monomers are used together, polymers to be formed on the substrate are copolymers. Either embodiment is included in the present invention. In addition, monomers other than the ones described above may be further added for copolymerization when T needs to be adjusted in accordance with the type of proliferated cells, when a necessity arises to enhance interaction between the coated material and cell culture support, or when the balance between hydrophilicity and hydrophobicity of the cell support needs to be adjusted and the like. Furthermore, graft or block copolymers of the above polymers to be used in the present invention and other polymers, or mixtures of the polymers of the present invention and other polymers may also be used. Moreover, crosslinking may also be performed as long as it does not impair the original properties of the polymers.

For pH responsive polymers and ion responsive polymers, the ones suitable for a cell sheet to be manufactured may be arbitrarily selected.

[Coating Composition]

For the method of the present invention, a coating composition including a monomer which can form the aforementioned environment responsive polymer by polymerization by radiation irradiation and an organic solvent is used. Furthermore, an oligomer or prepolymer formed by polymerization of the aforementioned monomer is preferably added to the aforementioned coating composition to be used. Crystallization can be suppressed by using a coating composition including the oligomer or prepolymer even in the case with a small amount of an organic solvent. Therefore, a uniform environment responsive polymer layer can be formed all over the substrate surface by coating the substrate surface with this coating composition and by facilitating polymerization by radiation irradiation.

The monomer for radiation polymerization is as described above. The coating composition includes one or more kinds of monomers.

The size of the oligomer or prepolymer contained in the coating composition is not specifically limited as long as it is larger than or equal to that of a dimer. Preferred are the ones whose molecular weight is larger than approximately 3300 (typically a 28-molecule polymer), and more preferred are the ones whose molecular weight is 5700 or more. The upper limit is not specifically limited, and the molecular weight can be one million or more. Meantime, the term "prepolymer" used in the present invention refers to a polymer prior to radiation irradiation.

The organic solvent is not specifically limited as long as it can dissolve the monomer, oligomer or prepolymer. Preferred are the ones whose boiling temperatures are 120° C. or lower, and more preferred are the ones whose boiling temperatures are in the range of 60 to 110° C. at normal pressure. Examples of preferred solvents include methanol, ethanol, n (or i)-propanol, 2 (or n)-butanol and water. One or more of these may be used. One or more solvents other than these such as 1-pentanol, 2-ethyl-1-butanol, 2-butoxyethanol, and ethylene (or diethylene) glycol or monoethyl ether thereof may also be used. Other additives such as acids as exemplified by sulfuric acid and Mohr's salt may be formulated in the above solution.

The amount of the monomer contained in the coating composition is preferably in the range of 5 to 70 wt %.

When the coating composition further contains an oligomer or prepolymer, the amount of the oligomer or prepolymer contained in the aforementioned composition is preferably in the range of 0.1 to 20 wt %. The weight ratio of the monomer and the oligomer or prepolymer contained in the aforementioned composition is preferably in the range of 500:1 to 1:20.

The viscosity of the coating composition is preferably in the range of $5 \times 10^{-3}$ Pa·s to 10 Pa·s.

[Substrate]

[Substrate for the First Invention]

The substrate to be coated with the coating composition is not specifically limited as long as the surface thereof contains a material which can be covalently bonded to the aforementioned responsive polymer by radiation irradiation. The substrate may contain a material which can be covalently bonded to aforementioned responsive polymer by radiation irradiation only on the surface or, alternatively, the entire substrate may contain such material. The material of such substrate may be glasses, plastics, ceramics, metals and the like which are generally used for cell culture, but not specifically limited as long as it is a material which enables cell culture. The surface or an inner layer of the substrate may be set up with an arbitrary layer and treated with an arbitrary treatment as long as they do not impede the object of the present invention. For example, hydrophilicity can be induced to the support surface with the use of treatment technologies such as ozone treatment, plasma treatment and sputtering.

Examples of material which construct the substrate and can be covalently bonded to the aforementioned responsive polymer itself include polystyrene, low-density polyethylene, medium-density polyethylene, high-density polyethylene, polyurethane, acrylic resins such as urethane acrylate and polymethylmethacrylate, polyamide (nylon), polycarbonate, natural rubber having covalent bonds, synthetic rubbers having covalent bonds, silicon rubbers containing polysilicon and microporous polycarbonate. The substrate may be a blend polymer or polymer alloy containing 2 or more of these materials.

Examples of substrate whose surface is treated to form covalent bonds with the aforementioned responsive polymer include polyethylene terephthalate whose surface is treated with an adhesion-improving treatment, a synthetic resin whose surface is processed with either corona treatment or plasma treatment, and a synthetic resin whose surface is coated with an acrylic resin such as urethane acrylate. The substrate may be a blend polymer or polymer alloy containing 2 or more of these materials. Examples of the synthetic resin include nylon, low-density polyethylene, medium-density polyethylene, polypropylene or polyethylene terephthalate, polycarbonate and polystyrene. The synthetic resin may be a blend polymer or polymer alloy including 2 or more of these materials.

Examples of the above described synthetic resin whose surface is processed with either corona treatment or plasma treatment include microporous nylon, microporous polyethylene, microporous polypropylene, microporous polyethylene terephthalate and microporous polycarbonate, whose surface is processed with either corona treatment or plasma treatment.

Examples of the shape of the substrate include dishes and films. When a film-shaped substrate is used, the substrate may be processed into a shape suitable for cell culture (such as a dish shape) after a graft polymer layer is formed on the surface of the film-shaped substrate. At the time of processing, a component composed of other materials may be used in combination with the aforementioned substrate if desired. When a dish-shaped substrate is used, at least the inner bottom surface region of the dish, which will serve as a cell adhesion surface, may be coated with the graft polymer layer.

[Substrate for the Second Invention]

The substrate to be coated with the coating composition in the present invention is a substrate which has a surface which can be covalently bonded to at least one environment responsive polymer selected from the group consisting of a temperature responsive polymer, a pH responsive polymer and an ion responsive polymer by radiation irradiation, and includes at least one material selected from the group consisting of polyethylene terephthalate whose surface is treated with an adhesion-improving treatment, synthetic resin whose surface is processed with either corona treatment or plasma treatment, and synthetic resin whose surface is coated with an acrylic resin, a natural rubber having covalent bonds, a synthetic rubber having covalent bonds, a silicon rubber containing polysilicon and microporous polycarbonate. The substrate has at least one surface (cell adhesion surface) which can form a cell sheet by culturing cells, wherein at least the cell adhesion surface is formed by the aforementioned material. Of course, the entire substrate may be composed of the aforementioned material. Examples of the shape of the substrate include dishes and films. When a film-shaped substrate is used, the substrate may be processed into a shape suitable for cell culture (such as a dish shape) after a graft polymer layer of an environment responsive polymer is formed on the surface of the film-shaped substrate. At the time of processing, a component composed of other materials may be used in combination with the aforementioned substrate if desired. When a dish-shaped substrate is used, at least the inner bottom surface region of the dish, which will serve as a cell adhesion surface, may be coated with the graft polymer layer.

As for the material of the substrate, polyethylene terephthalate whose surface is treated with an adhesion-improving treatment can be preferably used. Polyethylene terephthalate is being excellent in transparency, dimension stability, mechanical property, electric property, chemical resistance and the like and, thus, is preferred as the material of a cell support. Examples of "polyethylene terephthalate whose surface is treated with an adhesion-improving treatment" which can be used in the present invention include polyethylene terephthalate on which an adhesion-improved layer is formed by an adhesion-improving agent such as polyester, acrylic acid ester, polyurethane, polyethylenimine, and a silane coupling agent. To provide improved adhesiveness to a polyethylene terephthalate film, an adhesion-improving coating material is applied for coating through the inline coating or offline coating. The adhesion-improving coating material can be exemplified by a combination of the aforementioned adhesion-improving agent and a melamine series resin which is a crosslinking component. The inline coating is a method for applying a coating material during the film forming step of a film, and the offline coating method is a method for applying and drying a coating material by using a coater to process a biaxially-stretched polyethylene terephthalate film obtained by film forming. The inline coating is preferred in view of cost considerations. Examples of the method for applying the coating material include arbitrary coating methods such as roll coating, gravure coating, microgravure coating, reverse coating, reverse gravure coating, bar coating, roll brush method, air knife coating, curtain coating and die coating. The coating method may be arbitrarily used alone or in combination.

Synthetic resin whose surface is processed with either corona treatment or plasma treatment may also be preferably used as the material of the substrate. Examples of synthetic resin which can be used in this case include nylon, low-density polyethylene (which refers to polyethylene whose density is 910 Kg/m$^3$ or more and less than 930 Kg/m$^3$), medium-density polyethylene (which refers to polyethylene whose density is 930 Kg/m$^3$ or more and less than 942 Kg/m$^3$), polypropylene, polyethylene terephthalate, polycarbonate or polystyrene, or a blend polymer or polymer alloy including 2 or more of these materials.

As for the material of the substrate, a microporous material composed of nylon, polyethylene, polypropylene, polyethylene terephthalate or polycarbonate, or a blend polymer or polymer alloy including 2 or more of these materials, wherein the surface thereof is processed with either corona treatment or plasma treatment, may also be preferably used. As far as microporous polycarbonate, one having a surface not being processed with either corona treatment or plasma treatment may also be preferably used. Such microporous material can be effectively covalently bonded to an environment responsive polymer without impairing medium permeability. In such cases, the substrate is preferably in film-shape. A film-shaped microporous substrate is preferably used for an insert culture.

The pore size and pore density of the aforementioned microporous material may be arbitrarily selected within the suitable range for a cell culture insert and the like. When the microporous membrane is used for a cell migration/infiltration assay which takes advantage of cells passing through the pores, the pore diameter needs to be large enough to allow the cells to pass through. In addition, when the porous membrane is used for a three-dimensional culture, co-culture for 2 kinds of cells and drug penetration assay, the pore size φ is preferably 20μ or less so that the cells are not allowed to migrate/infiltrate. Moreover, when a cell sheet composed of cells cultured to confluence is detached with the use of an environment responsive polymer, the pore size φ is preferably 20μ or less to prevent cell migration/infiltration, and is preferably 3μ or less so that the cell sheet is smoothly detached without becoming entangled in the pores. Furthermore, the material, thickness and pore density of the porous membrane affect the time required for a medium to pass through and, thus, are preferably fit to the desired cell culture insert.

As for the material of the substrate, a synthetic resin whose surface is coated with an acrylic resin can also be preferably used. By using such a synthetic resin, coating with a coating agent can be facilitated, and the graft ratio in graft polymerization by radiation irradiation can be elevated. In such cases, the ones similar to the synthetic resin, which is used for being processed with either corona treatment or plasma treatment, can be preferably used. Preferred acrylic resin is urethane acrylate.

As for the material of the substrate, a natural rubber having covalent bonds, a synthetic rubber having covalent bonds and a silicon rubber containing polysilicon can also be preferably used. These may be arbitrarily subjected to surface treatment. Radical dissociation of covalent bonds and proton emission induced by radiation irradiation easily occur on such materials and, thus, graft polymerization can be easily performed. Preferred natural rubbers having covalent bonds are the substances consisting primarily of cis-polyisoprene [(C$_5$H$_8$)$_n$], which is included in the sap of rubber trees. Examples of preferred synthetic rubber having covalent bonds include polybutadiene series, butadiene-acrylonitrile series, chloroprene series and ethylene propylene series. As for the silicon rubber containing polysilicon, the ones include the following basic unit are preferred:

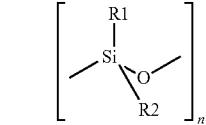

[Formula 1]

[Coating Step]

The method of the present invention includes a coating step in which the aforementioned coating composition is coated onto the surface of the aforementioned substrate to form a film on the surface.

The coating amount of the film formed in the present step may be 50 mg/m$^2$ or more, which is the amount required for an environment responsive graft polymer to exert its functions (such as temperature responsiveness). The upper limit of the coating amount is not specifically limited, but it is preferably less than 40 g/m$^2$, and more preferably less than 10 g/m$^2$. When the coating amount is 40 g/m$^2$ or more, the present inventors confirmed that the thickness of the film becomes unstable as the thickness thereof increases, the penetration and irradiance level of radiation becomes unstable due to the increase in thickness, and the coating amount of the graft polymer lacks in uniformity due to the convection flow within the film owning to radiation energy. In addition, the coating amount is preferably 10 g/m$^2$ or less in order to reduce the washing time to wash away ungrafted free polymers.

Any publicly known method can be used as a method for applying the coating composition to a small area of the substrate. Examples of the method include coating methods by a spin coater, bar coater and the like, and the spray coating method. Examples of coating method for coating a large area include blade coating, gravure coating, rod coating, knife coating, reverse roll coating and offset gravure coating.

In relation to solid formation, publicly known coating methods such as gravure coating, roll coating, slot coating, kiss coating, spray coating and fountain coating can be used for the formation. In addition, with regards to pattern formation of the graphic layer, publicly known printing methods such as gravure printing, screen printing and offset printing can be used. Continuous coating method or printing method can be used as the method for applying the coating composition to the substrate. More specifically, as for the continuous coating method or printing method, coating methods such as hot melt coating, hot lacquer coating, gravure direct coating, gravure reverse coating, die coating, microgravure coating, slide coating, slit reverse coating, curtain coating, knife coating, air coating and roll coating can be used. It is to be noted that these are given for purposes of exemplification, and those skilled in the art can tentatively use an applicable method.

[Radiation Irradiation Step]

The method of the present invention includes a radiation irradiation step wherein the polymerization reaction which forms the aforementioned environment responsive polymer and the binding reaction (namely, grafting) which binds the aforementioned environment responsive polymer and the substrate surface are proceeded by irradiating radiation to the aforementioned film. As used herein, the term "binding reaction (grafting)" includes not only the phenomenon wherein free polymers, which are formed in situ from monomers, oligomers or prepolymers by polymerization by radiation irradiation, bind to the substrate surface but also the phenomenon wherein the polymer chain elongates originating from the aforementioned monomers after free monomers bind to the substrate surface, the phenomenon wherein the coating composition-derived free prepolymers or oligomers bind to the substrate surface, and the phenomenon wherein the polymer chain elongates originating from the polymers or oligomers bound to the substrate surface and the like.

Examples of radiation to be used include α rays, β rays, γ rays, electron beam and ultraviolet rays. To manufacture the desired graft polymer, γ rays and electron beam are preferred because they have high energy efficiency and electron beam is particularly preferred in terms of their productivity. With regards to ultraviolet rays, they can be used in combination with a suitable polymerization initiation agent or an agent anchoring to the substrate.

The radiation dosage is preferably in the range of 5 Mrad to 50 Mrad for electron beam, or in the range of 0.5 Mrad to 5 Mrad for γ rays.

When a coating composition including oligomers or prepolymers whose polymerization is proceeded to some extent is used as the coating composition, it is possible to complete the formation of an environment responsive polymer by polymerization and the grafting reaction between the substrate surface and the environment responsive polymer only by a single shot irradiation of radiation.

[Drying Step]

The method of the present invention includes a drying step to remove the organic solvent derived from the coating composition by drying the aforementioned film.

The film which is formed by the aforementioned coating step does not form crystals under the influence of the amount of residual solvent and, thus, drying may be performed after irradiating radiation to the film before drying or, alternatively, radiation irradiation may be performed after drying the film. Nevertheless, it is preferred to irradiate radiation after drying the film because a wet film prior to drying may be influenced by environmental changes, foreign substances, fluctuation in thickness of the film and the like if being subjected to radiation irradiation.

The method of drying is not specifically limited, but typical examples include dry air drying, hot air (warm air) drying and (far) infrared drying.

[Washing Step]

In the environment responsive polymer layer of the cell culture support formed through each of the above mentioned steps, not only the polymer molecules immobilized via covalent bonding to the substrate surface but also unimmobilized free polymer molecules and unreacted monomer molecules are present. In addition, when a coating composition containing oligomer or prepolymer molecules is used, unreacted oligomer molecules or prepolymer molecules may further be present in the environment responsive polymer layer. Consequently, the method of the present invention preferably further includes a washing step to perform washing in order to remove these free polymers and unreacted substances.

The method of washing is not specifically limited, but typical examples include immersion washing, swing washing, shower washing, spray washing and ultrasonic washing. In addition, examples of a washing solution typically include various water-based ones, alcohol-based ones, hydrocarbon-based ones, chlorine-based ones and acid/alkali washing solutions. The combination of a washing method and a washing solution may be arbitrarily selected in accordance with the cell culture support to be washed.

[Cell Culture Support Manufactured by the Method of the Present Invention]

The present invention also relates to a cell culture support manufactured by the method of the present invention.

The thickness of the graft polymer layer immobilized onto the surface of the cell culture support of the present invention is preferably in the range of 0.001 to 10 μm when dried.

In addition, the coating amount of various environment responsive polymers on the surface of the cell culture support is preferably in the range of 5 to 80 μg/cm$^2$, and more preferably 6 to 40 μg/cm$^2$. When the coating amount of an environment responsive polymer exceeds 80 μg/cm$^2$, cells are not adhered to the surface of the cell culture support. Conversely, when the coating amount is less than 5 μg/cm$^2$, cells are cultured in single layer conditions and not formed into a tissue, and it becomes difficult to detach cultured cells from the support. Such coating amount of an environment responsive polymer can be measured by using, for example, Fourier transform infrared spectrometer attenuated total reflection (FT-IR-ATR method), analysis by staining the coated region or non-coated region, or staining of fluorescent substances and, further more, surface analysis by contact angle measurements and the like either alone or in combination.

The cell culture support manufactured by the method of the first invention has a uniform graft polymer layer in comparison with the cell culture support manufactured by the conventional method using a material monomer/solvent mixture as the coating composition.

The cell culture support manufactured by the method of the second invention comprises a substrate including at least one material selected from the group consisting of polyethylene terephthalate whose surface is treated with an adhesion-improving treatment, synthetic resin whose surface is processed with either corona treatment or plasma treatment, and synthetic resin whose surface is coated with an acrylic resin, natural rubber having covalent bonds, synthetic rubber having covalent bonds, silicon rubber containing polysilicon and microporous polycarbonate, wherein the aforementioned environment responsive polymer is immobilized onto the surface thereof by covalent bonding.

[Method for Manufacturing a Cell Culture Sheet]

With the use of the cell culture support of the present invention, a cell sheet can be manufactured from various cells such as epithelial cells and endothelial cells constituting each tissue and organ within an organism, skeletal muscle cells, smooth muscle cells and cardiac muscle cells exhibiting contractility, neurons and glial cells constituting the nerve system, fibroblasts, hepatic parenchymal cells, hepatic non-parenchymal cells and adipocytes involving in the body's metabolism, stem cells present in various tissues, marrow cells and ES cells as cells having differential potency. The cell sheet manufactured by this method is suitable for use in regenerative medicine and the like because the adhesive factors on the surface thereof are not impaired and, in addition, the region adhered to the cell culture surface has uniform quality. With the use of the cell sheet, its applications to detection devices such as a biosensor can be expected.

EXAMPLES

Example 1

Preparation of Polyisopropylacrylamides Having Various Molecular Weights

Commercially available polyisopropylacrylamides having the following molecular weights were purchased.

TABLE 1.1

| | Molecular weight | Manufacturer | Part number |
|---|---|---|---|
| 1 | 5700 | POLYMER SOURCE, INC. | P3241 |
| 2 | 20000-25000 | ALDRICH Corporation | 535311 |
| 3 | 40000 or less | POLYMER SCIENCE, INC. | 21458-10 |
| 4 | 258000 | POLYMER SOURCE, INC. | P7142 |
| 5 | 300000 | SCIENTIFIC POLYMER PRODUCTS, INC. | 963 |

Preparation of Redox-Synthesized Polyisopropylacrylamide 17.8 g of N-isopropylacrylamide and 150 mL of purified water were charged in a 500 mL separable flask, to form a solution/dispersion under stirring. Under a nitrogen gas stream, 0.24 g of ammonium persulfate and 0.30 mL of N,N,N',N'-tetramethylethylenediamine were added at room temperature to initiate polymerization. After completion of polymerization, the mixture was heated to take out the gel, and the gel was dried in an electric drying apparatus at 100° C. The dried gel was ground and subjected to GPC analysis in NMP solvent to find that the molecular weight was approximately 350 thousand to 400 thousand in comparison with commercially available items 1, 2 and 4.

Synthesis of Polyisopropylacrylamide With the Use of a Chain Transfer Agent

Low molecular weight polyisopropylacrylamide and isopropylacrylamide oligomer were synthesized in accordance with Non-Patent Document 3 with the use of n-butyl mercaptan as a chain transfer agent. Polymer synthesis: 11.3 g of N-isopropylacrylamide and 300 mL of benzene were charged in a 1 L separable flask to form a solution/dispersion under stirring. Under a nitrogen gas stream, either (a) 4.31 mL of n-butyl mercaptan or (b) 40 mL of a 0.1 M n-butyl mercaptan benzene solution was added to prepare a mixture, respectively. The total volume was brought up to 400 mL with a solution in which 1.2 g of benzoyl peroxide was dissolved in benzene to initiate polymerization. After completion of the reaction, the mixture was subjected to cold water extraction, and the extract was filtered through Sephadex G-25 gel available from Pharmacia Corp. to remove n-butyl mercaptan. Only the polymer fractions were then freeze-dried to give a synthetic polymer. Desulfurization of the product was conducted with the use of a Raney nickel catalyst, which is also described in Non-Patent Document 4. The polymer obtained under Condition (a) was determined as a 5-molecule polymer (molecular weight 650), and the polymer obtained under Condition (b) was determined as a 28-molecule polymer (molecular weight 3300). Based on these results, the following experiments were conducted.

Manufacture of Cell Culture Support

Test Example 1.1

As Examples 1.1 through 1.8, 0.1 mL of a solution, in which commercially available polyisopropylacrylamides 1 through 5 shown in Table 1.1 (Examples 1.1 through 1.5), redox-synthesized polyisopropylacrylamide (Example 1.6), synthetic polyisopropylacrylamide (a) with the use of a chain transfer agent (Example 1.7) or synthetic polyisopropylacrylamide (b) with the use of a chain transfer agent (Example 1.8) was dissolved to a concentration of 1 wt % respectively, and isopropylacrylamide monomer was dissolved to a concentration 40 wt % in isopropyl alcohol, was added to a 1008 Petri dish (Becton, Dickinson and Company) at room temperature of 25° C. and 60% humidity. As Comparative Example 1.1, an isopropyl alcohol solution containing 40 wt % isopropylacrylamide monomer without the polymers used in Examples was similarly added to prepare a dish. When these solutions were left to stand for 1 hour, the crystals were precipitated out in Comparative Example 1.1 as shown in Table 1.2, but were not in Examples 1.1 through 1.6 and 1.8. In Example 1.7, there were cases where the crystals were or were not precipitated out, and the microcrystals were observed under the microscope. Secondly, when the amount of each of these solutions to be added was changed to 0.03 mL, and each was added to a dish standing still in a horizontal position, the bottom of the dish was coated with the solution in 5 seconds or less. After 10 minutes, the crystals were precipitated out in Comparative Example 1.1 as shown in Table 1.2. The crystals were likewise not precipitated out in Examples 1.1 through 1.6 and 1.8. In Example 1.7, there were cases where the crystals were or were not precipitated out, and the microcrystals were observed under the microscope.

TABLE 1.2

| | Coating amount 0.1 mL (60 g/m$^2$), left to stand at room temperature for 1 hour | Coating amount 0.03 mL (20 g/m$^2$), left to stand at room temperature for 10 minutes |
|---|---|---|
| Example 1.1 | No crystal precipitation | No crystal precipitation |
| Example 1.2 | No crystal precipitation | No crystal precipitation |
| Example 1.3 | No crystal precipitation | No crystal precipitation |
| Example 1.4 | No crystal precipitation | No crystal precipitation |
| Example 1.5 | No crystal precipitation | No crystal precipitation |
| Example 1.6 | No crystal precipitation | No crystal precipitation |
| Example 1.7 | Microcrystal precipitation | Microcrystal precipitation |
| Example 1.8 | No crystal precipitation | No crystal precipitation |
| Comparative Example 1.1 | Crystal precipitation | Crystal precipitation |

Test Example 1.2

Next, the same solutions were prepared for Examples 1.1 through 1.6 to coat a 130 μm-thick biaxially-stretched polystyrene sheet (which is in widespread use as an OPS/antifog product and, thus, the antifog agent was removed with ethanol and dried prior to use) by a No. 4 wire bar in coating thickness of approximately 5 g/m$^2$. The resulting coating was dried with a dryer and drying under reduced pressure at 40° C. and 1×10$^2$ Pa for 1 minute, and then the states of the dried surfaces were examined. With the dryer drying, all the surfaces of the films were transparent, flat and smooth, and the microcrystals were not precipitated out in Examples 1.1 through 1.6 as shown in Table 1.3. The film was whitened with crystals, and flatness and smoothness of the film was partly damaged in Comparative Example 1.1. With the drying under reduced pressure at 40° C. and 1×10$^2$ Pa for 1 minute, although all the surfaces of the films were transparent, flat and smooth in Examples 1.1 through 1.6, the microcrystals were observed only in Example 1.1. The film was whitened with crystals and almost detached from the sheet in Comparative Example 1.1. When the amount of the polymer in Example 1.1 was reduced to 0.5% and raised to 2% and 5%, the frequency of precipitation of the microcrystals was inversely proportional to the amount of the polymer added.

TABLE 1.3

| | Coating amount 5 g/m$^2$, dried with a dryer | Coating amount 5 g/m$^2$, dried under reduced pressure at 40° C. and 1 × 10$^2$ Pa for 1 minute |
|---|---|---|
| Example 1.1 | No crystal precipitation | Microcrystal precipitation |
| Example 1.2 | No crystal precipitation | No crystal precipitation |

TABLE 1.3-continued

|  | Coating amount 5 g/m², dried with a dryer | Coating amount 5 g/m², dried under reduced pressure at 40° C. and 1 × 10² Pa for 1 minute |
|---|---|---|
| Example 1.3 | No crystal precipitation | No crystal precipitation |
| Example 1.4 | No crystal precipitation | No crystal precipitation |
| Example 1.5 | No crystal precipitation | No crystal precipitation |
| Example 1.6 | No crystal precipitation | No crystal precipitation |
| Comparative Example 1.1 | Crystal precipitation, whitened | Crystal precipitation, whitened |

Test Example 1.3

Subsequently, Petri dishes were coated with either 0.1 mL or 0.03 mL of the solutions used in Examples 1.1 through 1.8 and Comparative Example 1.1, and an electron beam was then irradiated in 2 shots. The irradiance level was 5 Mrad for the first shot and 25 Mrad for the second shot. After electron beam irradiation, ion-exchange water at 5° C. was used to wash the Petri dishes, and the residual monomers and monomers unbound to the surface of the Petri dishes were removed. The Petri dishes were then dried in a clean bench, and were subjected to ethylene oxide (EO) gas sterilization. By further performing sufficient deaeration, a cell culture support was obtained as the final product. Flatness and smoothness of the coated surfaces thereof were examined by checking for irregularity on the surfaces under the optical microscope. The results are shown in Table 1.4.

Bovine aortic endothelial cells were cultured on the obtained cell culture support material, using Dulbecco's Modified Eagle medium (DMEM) which contained 10% fetal calf serum (FCS) as the medium in 5% carbon dioxide at 37° C. After confirming that the cells were sufficiently proliferated, the medium was transferred into a chamber under 5% $CO_2$ at 20° C. with the support. After being left to stand for 30 minutes, the cells adhered and proliferated were detached. Cell proliferation and detachment recovery rates were calculated in accordance with the following formula, and the results are shown in Table 1.4:

Cell proliferation and detachment recovery rate(%)= 100×(Total number of cells detached and recovered)/(Total number of cells proliferated).

In doing so, in order to measure the total number of cells detached and recovered and the total number of cell proliferated, the cells need to be separated from one another. Therefore, after cooling to 20° C. and being left to stand, the recovered cell mass was subjected to a trypsin-EDTA treatment to separate the cells from one another. Measurement of the total number of cells detached and recovered was then performed. In addition, the total number of cells proliferated was calculated by adding the total number of cells detached and recovered by the above method to the total number of cells detached from one another by a trypsin-EDTA treatment for the cells which were not detached even after cooling to 20° C. and being left to stand. Moreover, with regards to a cell sheet-like mass in which the entire cells except for the region surrounding the dish reached the confluence state after being cultured for 5 days in a chamber at 37° C., the culture medium was transferred into a chamber under 5% $CO_2$ at 20° C. along with the support, and a cut in the cell layer in the sub-confluence state surrounding the dish was made with a scalpel. Detachment of the cell sheet was then observed.

TABLE 1.4

|  | Coating amount 0.1 mL (60 g/m²) | | | Coating amount 0.03 mL (20 g/m²) | | |
|---|---|---|---|---|---|---|
|  | Flatness and smoothness of support surface | Cell proliferation and detachment recovery rate (%) | Observation of cell sheet detachment | Flatness and smoothness of support surface | Cell proliferation and detachment recovery rate (%) | Observation of cell sheet detachment |
| Example 1.1 | Flat and smooth | >90 | Entire cell sheet smoothly detached without deformation | Flat and smooth | >90 | Entire cell sheet smoothly detached without deformation |
| Example 1.2 | Flat and smooth | >90 | Entire cell sheet smoothly detached without deformation | Flat and smooth | >90 | Entire cell sheet smoothly detached without deformation |
| Example 1.3 | Flat and smooth | >90 | Entire cell sheet smoothly detached without deformation | Flat and smooth | >90 | Entire cell sheet smoothly detached without deformation |
| Example 1.4 | Flat and smooth | >90 | Entire cell sheet smoothly detached without deformation | Flat and smooth | >90 | Entire cell sheet smoothly detached without deformation |
| Example 1.5 | Flat and smooth | >90 | Entire cell sheet smoothly detached without deformation | Flat and smooth | >90 | Entire cell sheet smoothly detached without deformation |
| Example 1.6 | Flat and smooth | >90 | Entire cell sheet smoothly detached without deformation | Flat and smooth | >90 | Entire cell sheet smoothly detached without deformation |

TABLE 1.4-continued

| | Coating amount 0.1 mL (60 g/m²) | | | Coating amount 0.03 mL (20 g/m²) | | |
|---|---|---|---|---|---|---|
| | Flatness and smoothness of support surface | Cell proliferation and detachment recovery rate (%) | Observation of cell sheet detachment | Flatness and smoothness of support surface | Cell proliferation and detachment recovery rate (%) | Observation of cell sheet detachment |
| Example 1.7 | Irregular | >90 | Cells not adhered to certain region, cell sheet perforated when detached | Microcrystal induced after irradiation, smoothed by washing | 30-80 | Not detached as cell sheet |
| Example 1.8 | Flat and smooth | >90 | Entire cell sheet smoothly detached without deformation | Flat and smooth | >90 | Entire cell sheet smoothly detached without deformation |
| Comparative Example 1.1 | Irregular | >90 | Cells not adhered to certain region, cell sheet perforated when detached | Microcrystal induced after irradiation, smoothed by washing | 30-80 | Not detached as cell sheet |

Test Example 1.4

Stretched polyethylene OPS was coated with the solutions prepared similarly to Examples 1.1 through 1.6 and Comparative Example 1.1 by wire bar coating. The coated surfaces were dried with a dryer, and subjected to electron beam irradiation. The resulting surfaces were washed and dried by the same method used for the coated Petri dishes. The obtained sheets were attached to the bottom of a Petri dish using double-faced adhesive tape. Subsequently, EOG sterilization was likewise performed to give a cell culture support.

The electron beam irradiance level was either 15 Mrad or 25 Mrad, and the irradiation was conducted in a single shot. Petri dishes coated with either 0.1 mL or 0.03 mL in Comparative Example 1.1 were irradiated with a single shot of electron beam at the above irradiance level for comparison. In Examples 1.1 through 1.6 used for coating OPS, the coated surfaces remained transparent with both 15 Mrad and 25 Mrad of electron beam irradiance levels. However, deformation and contraction of the sheet due to heat were observed with the irradiation at 25 Mrad. Deformation which disrupted the attachment of double-faced adhesive tape was observed at 30 Mrad. The recovery rate of cells grown in the cell culture and cell sheet detachment are shown in Table 1.5. Both the cells and the cell sheet were not detached at all at both irradiance levels in Comparative Example 1.1 in which the film was whitened with crystals. For the ones subjected to the irradiation in a wet state after coating the dishes, grossly-visible deformation of the dishes was not observed at both irradiance levels. Nevertheless, with the coating amount of 0.1 mL, although the cells were recovered at both irradiance levels, the recovery rate was low and the cells were not detached as a cell sheet. With the coating amount of 0.03 mL, the microcrystals were precipitated out, the cells were not recovered, and the cell sheets were not detached at both irradiance levels. With regards to Examples 1.1 through 1.6, the results were all favorable except for the fact that it took a long time for the cell sheet to be detached in Example 1.1.

TABLE 1.5

| | Electron beam irradiance level 15 Mrad | | | Electron beam irradiance level 25 Mrad | | |
|---|---|---|---|---|---|---|
| | Flatness and smoothness of support surface | Cell proliferation and detachment recovery rate (%) | Observation of cell sheet detachment | Flatness and smoothness of support surface | Cell proliferation and detachment recovery rate (%) | Observation of cell sheet detachment |
| Example 1.1 | Flat and smooth | >90 | Entire cell sheet smoothly detached without deformation | Flat and smooth | >90 | Entire cell sheet smoothly detached without deformation |
| Example 1.2 | Flat and smooth | >90 | Entire cell sheet smoothly detached without deformation | Flat and smooth | >90 | Entire cell sheet smoothly detached without deformation |
| Example 1.3 | Flat and smooth | >90 | Entire cell sheet smoothly detached | Flat and smooth | >90 | Entire cell sheet smoothly detached |

TABLE 1.5-continued

|  | Electron beam irradiance level 15 Mrad | | | Electron beam irradiance level 25 Mrad | | |
| --- | --- | --- | --- | --- | --- | --- |
|  | Flatness and smoothness of support surface | Cell proliferation and detachment recovery rate (%) | Observation of cell sheet detachment | Flatness and smoothness of support surface | Cell proliferation and detachment recovery rate (%) | Observation of cell sheet detachment |
| Example 1.4 | Flat and smooth | >90 | Entire cell sheet smoothly detached without deformation | Flat and smooth | >90 | Entire cell sheet smoothly detached without deformation |
| Example 1.5 | Flat and smooth | >90 | Entire cell sheet smoothly detached without deformation | Flat and smooth | >90 | Entire cell sheet smoothly detached without deformation |
| Example 1.6 | Flat and smooth | >90 | Entire cell sheet smoothly detached without deformation | Flat and smooth | >90 | Entire cell sheet smoothly detached without deformation |
| Comparative Example 1.1, Wire bar coat | Crystal induced before irradiation, smoothed by washing | Not detached at all | Not detached as cell sheet | Crystal induced before irradiation, smoothed by washing | Not detached at all | Not detached as cell sheet |
| Comparative Example 1.1, Coating amount 0.1 mL | Irregular | >90 | Cells not adhered to certain region, cell sheet perforated when detached | Irregular | >90 | Cells not adhered to certain region, cell sheet perforated when detached |
| Comparative Example 1.1, Coating amount 0.03 mL | Microcrystal induced after irradiation, smoothed by washing | Not detached at all | Not detached as cell sheet | Microcrystal induced after irradiation, smoothed by washing | Not detached at all | Not detached as cell sheet |

Test Example 1.5

In relation to Examples 1.2 and 1.6, 1 Kg of an isopropyl alcohol composition, in which the amount of the polymer contained was adjusted to either 0.5 wt %, 2 wt % or 5 wt % polymer and 40 wt % monomer was contained, was prepared respectively. A continuous base film in a roll shape composed of adhesive PET coated with an adhesive and protected by a detachment film was coated with a coating amount of 9 mg/m² at a rate of 5 m per minute, using a gravure direct roll sculptured 48 lines per centimeter. After drying in a hot air dryer having a one-meter-long hot air channel at 45° C., the resulting films were subjected to electron beam irradiation in an environment where the oxygen concentration was 50 ppm or less by using a continuous electron beam irradiation unit. The irradiance level was set to 10, 12, 16, 20 and 24 Mrad by changing the electronic flow of the electron beam. The film manufactured under each condition was washed, dried, and cut into dish-size pieces. Each piece was then immobilized onto a dish with an adhesive, and subjected to EOG sterilization to give a cell culture support.

All the cell culture supports manufactured from each composition had flat, smooth and transparent surfaces, and showed favorable cell recovery and cell sheet detachment as shown in Table 1.5. With regards to the composition containing 2 wt % polymer, a 200 m coating was conducted, and a cell culture support was manufactured from the film prepared at the end of the 40-minute coating period. The support showed no difference in terms of cell recovery and cell sheet detachment properties in comparison with the cell culture support from the film prepared in the early states of the coating period, and the results were favorable.

Test Example 1.6

As Example 1.9, a sample was manufactured without irradiating an electron beam when a continuous film is manufactured through the continuous coating, drying, electron beam irradiation steps of the above Example 1.2. This film was irradiated with γ rays emitted from cobalt-60 at 1.5 Mrad for 2 hours at room temperature. As described above, the resulting film was washed, dried, cut and attached to a dish. The resulting dish was subjected to EOG sterilization to give a cell culture support. All the cell culture supports had flat, smooth and transparent surfaces, and showed favorable cell recovery and cell sheet detachment.

Test Example 1.7

As Examples 1.10 through 1.16, the base films shown in Table 1.6 were coated with the composition prepared in Example 1.2 by wire bar (No. 4) coating. After dryer drying, the coated surfaces of the films were irradiated with an electron beam. The resulting dishes were washed and dried by the same method used for the coated Petri dishes. The irradiance level of an electron beam was either 10 Mrad, 15 Mrad or 25 Mrad, and the irradiation was conducted in a single shot. With the polystyrene film, the substrate temperature reached 70° C. with 25 Mrad irradiation, and a certain degree of deformation was observed similarly to Examples 1.1 through 1.6. With PET and polyimide, the substrate temperature also reached 70° C., but no deformation was observed owning to heat resistance of the substrates. With nylon, polyethylene and polypropylene, the substrate temperature did not rise and no deformation was observed. After washing and drying, the films were cut into circles, and each was attached to either the reverse side of the coating or the bottom of a Petri dish using double-faced adhesive tape. These were subjected to EOG sterilization to give cell culture supports. The self-prepared film of Example 1.12 was prepared by coating the film of Example 1.11 with the composition shown in Table 1.7 by wire bar (No. 4) coating and hardening the coated surface by irradiating ultraviolet rays under the conditions of 170 mJ/cm$^2$ (365 nm) with the use of a high pressure mercury lamp. The hardened coated surface was used as were other films. For the polystyrene film prepared in Comparative Example 1.2, the antifog agent was removed with ethanol and dried prior to use.

TABLE 1.6

| | Film name | Manufacturer | Part number |
|---|---|---|---|
| Example 1.10 | Polyester (PET) | TORAY INDUSTRIES, INC. | Rumilar 100T60 |
| Example 1.11 | Adhesive PET | TORAY INDUSTRIES, INC. | Rumilar U35 |
| Example 1.12 | Urethane acrylate | *Self-prepared | |
| Example 1.13 | Nylon | UNITICA, LTD. | ONU-15-200 |
| Example 1.14 | Polyethylene (low density) | DNP TECHNO FILM CO., LTD. | M16P #60 |
| Example 1.15 | Polyethylene | DNP TECHNO FILM CO., LTD. | MP-A #60 |
| Example 1.16 | Polyimide | DU PONT CO. | KAPTON 100H |
| Comparative Example 1.2 | Polystyrene | MITSUBISHI CHEMICAL CORP. | OPS conventional antifog product #130 |

TABLE 1.7

Formulation of urethane acrylate coating composition

| | |
|---|---|
| Urethane acrylate (The Nippon Synthetic Chemical Industry Co., Ltd.), product name: "Gohselac UV-7500B") | 45 parts |
| 1,6-hexanediol diacrylate (NIPPON KAYAKU CO., LTD.) | 40 parts |
| Pentaerythritol triacrylate (TOAGOSEI CO., LTD.) | 11 parts |
| 1-hydroxycyclohexyl phenyl ketone (CIBA SPECIALTY CHEMICALS, INC., product name: "IRGACURE 184") | 2 parts |
| Benzophenone (NIPPON KAYAKU CO., LTD.) | 2 parts |

By the same method as described in Examples 1.1 through 1.8, measurements of the recovery rates of cells and observations of cell sheet detachment were conducted. As the results shown in the following Table 1.8, neither cell recovery nor cell sheet detachment was observed with polyimide. With polyester, the recovery rate and cell sheet detachment were both weaker as a functional support than those of polystyrene. With adhesive PET, urethane acrylate, nylon, low-density polyethylene (LDPE), the supports manufactured with a lower radiation dosage showed the functions in comparison with polystyrene.

TABLE 1.8

| | 10 Mrad | | 15 Mrad | | 25 Mrad | |
|---|---|---|---|---|---|---|
| | Recovery rate (%) | Observation of cell sheet detachment | Recovery rate (%) | Observation of cell sheet detachment | Recovery rate (%) | Observation of cell sheet detachment |
| Example 1.10 | <20 | Sheet not detached | 30-80 | Sheet not detached | 30-80 | Sheet not detached |
| Example 1.11 | >90 | Partly detached | >90 | Overall favorable | >90 | Overall favorable |
| Example 1.12 | >90 | Partly detached | >90 | Overall favorable | >90 | Overall favorable |
| Example 1.13 | >90 | Partly detached | >90 | Overall favorable | >90 | Overall favorable |
| Example 1.14 | >90 | Partly detached | >90 | Overall favorable | >90 | Overall favorable |
| Example 1.15 | 30-80 | Sheet not detached | >90 | Partly detached | >90 | Overall favorable |
| Example 1.16 | <20 | Sheet not detached | <20 | Sheet not detached | <20 | Sheet not detached |
| Comparative Example 1.2 | 30-80 | Sheet not detached | >90 | Overall favorable | >90 | Overall favorable |

Example 2

Test Example 2.1

Tests were conducted for 2 kinds of prepolymers of temperature responsive polymers.

Polyisopropylacrylamide having a molecular weight in the range of 20000 to 25000 which was commercially available from Sigma-Aldrich Co., Ltd (ALDRICH Corporation, Part Number 535311) was used as Prepolymer 1 for the following experiments.

Polyisopropylacrylamide obtained by performing a redox synthesis according to the following procedure was used as Prepolymer 2 for the following experiments. 17.8 g of N-isopropylacrylamide and 150 mL of purified water were charged in a 500 mL separable flask to form a solution/dispersion under stirring. Under a nitrogen gas stream, 0.24 g of ammonium persulfate and 0.30 mL of N,N,N',N'-tetramethylethylenediamine were added at room temperature to initiate polymerization. After completion of polymerization, the mixture was heated to take out the gel, and the gel was dried in an electric drying apparatus at 100° C. to give Prepolymer 2. The dried gel was ground and subjected to GPC analysis in NMP solvent to find that the molecular weight was approximately 350 thousand to 400 thousand in comparison with the above Prepolymer 1, polyisopropylacrylamide manufactured by Polymer Source, Inc., Part Number P3241 (molecular weight 5700) and polyisopropylacrylamide manufactured by Polymer Source, Inc., Part Number P7142 (molecular weight 258000).

1 Kg of a solution in which Prepolymer 1 was dissolved to a concentration of 0.5 wt % and isopropylacrylamide monomer was dissolved to a concentration of 40 wt % in isopropyl alcohol was prepared. This solution was used as Coating Composition 1.

1 Kg of a solution in which Prepolymer 1 was dissolved to a concentration of 2 wt % and isopropylacrylamide monomer was dissolved to a concentration of 40 wt % in isopropyl alcohol was prepared. This solution was used as Coating Composition 2.

1 Kg of a solution in which Prepolymer 1 was dissolved to a concentration of 5 wt % and isopropylacrylamide monomer was dissolved to a concentration of 40 wt % in isopropyl alcohol was prepared. This solution was used as Coating Composition 3.

1 Kg of a solution in which Prepolymer 2 was dissolved to a concentration of 0.5 wt % and isopropylacrylamide monomer was dissolved to a concentration of 40 wt % in isopropyl alcohol was prepared. This solution was used as Coating Composition 4.

1 Kg of a solution in which Prepolymer 2 was dissolved to a concentration of 2 wt % and isopropylacrylamide monomer was dissolved to a concentration of 40 wt % in isopropyl alcohol was prepared. This solution was used as Coating Composition 5.

1 Kg of a solution in which Prepolymer 2 was dissolved to a concentration of 5 wt % and isopropylacrylamide monomer was dissolved to a concentration of 40 wt % in isopropyl alcohol was prepared. This solution was used as Coating Composition 6.

A continuous base film in a roll shape composed of adhesive polyethylene terephthalate (PET) coated with an adhesive and protected by a detachment film was coated with a coating amount of 9 mg/m$^2$ of Coating Compositions 1 through 6, respectively, at a rate of 5 m per minute, using a gravure direct roll sculptured 48 lines per centimeter. After drying in a hot air dryer having a one-meter-long hot air channel at 45° C., the resulting films were subjected to electron beam irradiation in an environment where the oxygen concentration was 50 ppm or less by using a continuous electron beam irradiation unit. The irradiance level was set to 10, 12, 16, 20 and 24 Mrad by changing the electronic flow of the electron beam. After electron beam irradiation, ion-exchange water at 5° C. was used to wash the films, and the residual monomers and polyomers unbound to the surface of the films were removed. The resulting films were then dried in a clean bench, and were subjected to ethylene oxide gas (EOG) sterilization. Sufficient deaeration was further performed to give the films. Flatness and smoothness of the coated surfaces thereof were examined by checking for irregularity on the surfaces under the optical microscope. All the coated surfaces (cell culture surfaces) of the films manufactured with the use of Coating Compositions 1 through 6 had flat, smooth and transparent surfaces.

The films manufactured with the use of Coating Compositions 1 through 6 were cut into dish-size pieces. Each piece was then immobilized onto the inner bottom surface of a dish with its coated surface up using an adhesive, and was subjected to EOG sterilization. The cell culture supports obtained by the method were used to perform a bovine aortic endothelial cell culture. More specifically, on the cell culture support, a culture of the aforementioned cells was conducted using Dulbecco's Modified Eagle medium (DMEM) which contained 10% fetal calf serum (FCS) as the medium in 5% carbon dioxide at 37° C. After confirming that the cells were sufficiently proliferated, the medium was transferred into a chamber under 5% $CO_2$ at 20° C. along with the dish. After being left to stand for 30 minutes, the cells adhered and proliferated are detached. Cell proliferation and detachment recovery rates were calculated in accordance with the following formula. It was defined as follows: Cell proliferation and detachment recovery rate (%)=100×(Total number of cells detached and recovered)/(Total number of cells proliferated). In doing so, in order to measure the total number of cells detached and recovered and the total number of cell proliferated, the cells need to be separated from one another. Therefore, after cooling to 20° C. and being left to stand, the recovered cell mass was subjected to a trypsin-EDTA treatment to separate the cells from one another. Measurement of the total number of cells detached and recovered was then performed. In addition, the total number of cells proliferated was calculated by adding the total number of cells detached and recovered by the above method to the total number of cells detached from one another by a trypsin-EDTA treatment for the cells which were not detached even after cooling to 20° C. and being left to stand. Moreover, with regards to a cell sheet-like mass in which the entire cells except for the region surrounding the dish reached the confluence state after being cultured for 5 days in a chamber at 37° C., the culture medium was transferred into a chamber under 5% $CO_2$ at 20° C. along with the dish, and a cut in the cell layer in the sub-confluence state surrounding the dish was made with a scalpel. Detachment of the cell sheet was then observed.

In the manufacture examples of cell sheets manufactured with the use of the cell culture supports prepared by using Coating Compositions 1 through 6, all showed high cell proliferation and detachment recovery rates exceeding 90%, and the cell sheets were able to be smoothly detached without deformation. With regards to the composition containing 2 wt % polymer (namely, Coating Compositions 2 and 5), a 200 m coating was conducted, and a cell culture support was manufactured from the film prepared at the end of the 40-minute coating period. The support showed no difference in terms of cell recovery and cell sheet detachment properties in comparison with the cell culture support from the film prepared in the early states of the coating period, and the results were favorable.

Test Example 2.2

In the present test example, a sample was manufactured without irradiating an electron beam when a continuous film was manufactured by using Coating Compositions 1, 2 or 3 described in Test Example 2.1. Thee films were irradiated with γ rays emitted from cobalt-60 at 1.5 Mrad for 2 hours at room temperature. Similarly to the procedure described in Test Example 2.1, each of the resulting film was washed, dried, cut and attached to a dish. The resulting dish was subjected to EOG sterilization to give a cell culture support. All the cell culture supports had flat, smooth and transparent surfaces, and showed favorable cell recovery and cell sheet detachments.

Test Example 2.3

As Examples 2.1 through 2.14, each of the base films shown in Table 2.1 was coated with a solution in which Prepolymer 1 described in Test Example 2.1 was dissolved to a concentration of 1 wt % and isopropylacrylamide monomer was dissolved to a concentration of 40 wt % in isopropyl alcohol (Coating Composition 7) by wire bar (No. 4) coating. After dryer drying, the coated surfaces of the films were irradiated with an electron beam. The resulting film was washed and dried by the same procedure as described in Test Example 2.1. The irradiance level of an electron beam was either 10 Mrad, 15 Mrad or 25 Mrad, and the irradiation was conducted in a single shot. After washing and drying, each of the films was cut into a circle, and the reverse side of the coating was attached to the inner bottom surface of a Petri dish using double-faced adhesive tape. This was then subjected to EOG sterilization to give a cell culture support. The obtained cell culture support was used to perform a bovine aortic endothelial cell culture by the same procedure as described in Test Example 2.1 to give a cell culture sheet. Subsequently, by the same procedure as described in Test Example 2.1, measurements of the recovery rates of cells and observations of cell sheet detachment were conducted.

The self-prepared film of Example 2.2 was prepared by coating the film of Example 2.1 with the composition shown in Table 2.2 by wire bar (No. 4) coating and hardening the coated surface by irradiating ultraviolet rays under the conditions of 170 mJ/cm$^2$ (365 nm) with the use of a high pressure mercury lamp. The hardened coated surface was used as were other films. For the polystyrene film prepared in Comparative Example 2.1, the antifog agent was removed with ethanol and dried prior to use.

For the films used in Examples 2.3 through 2.5, the ones having a corona treated surface for printing manufacturing were used, wherein the aforementioned corona treated surface was coated with a coating composition and irradiated with an electron beam. The films used in Examples 2.6 through 2.14 were processed with plasma treatment, and the obtained plasma treated surfaces were coated with a coating composition and irradiated with an electron beam. Plasma treatment was performed by a plasma discharge at 400 W for 3 minutes after filling oxygen under a reduced pressure vacuum of approximately 60 to 150 mmTorr. In relation to the synthetic rubbers used in Examples 2.12 through 2.14, the ones coated with a solution in which Prepolymer 1 described in Test Example 2.1 was dissolved to a concentration of 5 wt % and isopropylacrylamide monomer was dissolved to a concentration of 10 wt % in isopropyl alcohol (Coating Composition 8) by wire bar coating (B) were manufactured in addition to the ones coated with Coating Composition 7 by wire bar coating (A). In Example 2.15, a microporous polycarbonate used in Example 2.10 was processed without plasma treatment and evaluated by the same method. In Comparative Example 2.2, a microporous polyethylene used in Example 2.8 was processed without plasma treatment and evaluated by the same method.

TABLE 2.1

|  | Film name | Manufacturer | Part number |
|---|---|---|---|
| Example 2.1 | Adhesive polyester (PET) | TORAY INDUSTRIES, INC. | Rumilar U35 |
| Example 2.2 | Urethane acrylate | *Self-prepared |  |
| Example 2.3 | Nylon | UNITICA, LTD. | ONU-15-200 |
| Example 2.4 | Polyethylene (low density) | DNP TECHNO FILM CO., LTD. | M16P #60 |
| Example 2.5 | Polyethylene (medium density) | DNP TECHNO FILM CO., LTD. | MP-A #60 |
| Example 2.6 | Microporous polyethylene | TOKUYAMA CORP. | PORUM PH50 |
| Example 2.7 | Microporous polypropylene | TOKUYAMA CORP. | NF sheet NN100 |
| Example 2.8 | Microporous polyethylene | Asahi Kasei Chemicals Corp. | HIPORE NB630 |
| Example 2.9 | Microporous polyethylene | Asahi Kasei Chemicals Corp. | HIPORE H6022 |
| Example 2.10 | Microporous polycarbonate | WHATMAN PLC. | CYCLOPORE 7060-4704 |
| Example 2.11 | Microporous polycarbonate | WHATMAN PLC. | CYCLOPORE 7060-4713 |
| Example 2.12 | Polybutadiene |  | MB-1500 |
| Example 2.13 | Conjugated ethylene-propylene (EPR) |  | EP-5065 |
| Example 2.14 | Polysilicon | TORAY DOW CHEMICALS | IS-825 sheet #500 |
| Example 2.15 | Microporous polycarbonate (without plasma treatment) | WHATMAN PLC. | CYCLOPORE 7060-4704 |
| Comparative Example 2.1 | Polystyrene | MITSUBISHI CHEMICAL CORP. | OPS conventional antifog product #130 |
| Comparative Example 2.2 | Microporous polyethylene | Asahi Kasei Chemicals Corp. | HIPORE NB630 |
| Comparative Example 2.3 | Polyester (PET) | TORAY INDUSTRIES, INC. | Rumilar 100T60 |
| Comparative Example 2.4 | Polyimide | DU PONT CO. | KAPTON 100H |

TABLE 2.2

Formulation of urethane acrylate coating composition

| | |
|---|---|
| Urethane acrylate (Nippon Synthetic Chemical Industry Co., Ltd.), product name: "Gohselac UV-7500B") | 45 parts |
| 1,6-hexanediol diacrylate (NIPPON KAYAKU CO., LTD.) | 40 parts |
| Pentaerythritol triacrylate (TOAGOSEI CO., LTD.) | 11 parts |
| 1-hydroxycyclohexyl phenyl ketone (CIBA SPECIALTY CHEMICALS K.K., product name: "IRGACURE 184") | 2 parts |
| Benzophenone (NIPPON KAYAKU CO., LTD.) | 2 parts |

The results of measurements of the recovery rates of cells and observations of cell sheet detachment are shown in Tables 2.3. With polyimide, neither cell recovery nor cell sheet detachment was observed. With polyester, the recovery rate and cell sheet detachment were both weaker as a functional support than those of polystyrene. When adhesive PET, urethane acrylate, nylon or low-density polyethylene (LDPE) was used, the cell culture supports manufactured with a lower radiation dosage showed more favorable functions than when polystyrene was used.

detached. Due to a large pore size (in the range of 5 μm at maximum) in Example 2.9, the entire cell sheet was not detached as one favorable cell sheet although partial detachment was observed under all radiation conditions.

With regards to polysilicon, in contrast to the fact that the entire cells except for the region surrounding the dish reached the confluence state after being cultured for 5 days in a chamber at 37° C. with other cell culture supports manufactured under the same conditions, it took 8 days of culture to reach the same state in Example 2.14A. It took 5 days of culture for Example 2.14B to reach the confluence state.

With polystyrene film, the substrate temperature reached 70° C. with 25 Mrad irradiation, and a certain degree of deformation was observed. With PET and polyimide, the substrate temperature reached 70° C., but no deformation was observed owning to heat resistance of the substrates. With nylon, polyethylene, polypropylene, polybutadiene and polysilicon, the substrate temperature did not rise and no deformation was observed. With regards to Porum (microporous polyethylene), a certain degree of deformation was observed due to heat generated by calcium carbonate microparticles contained.

TABLE 2.3

| | 10 Mrad | | 15 Mrad | | 25 Mrad | |
|---|---|---|---|---|---|---|
| | Recovery rate (%) | Observation of cell sheet detachment | Recovery rate (%) | Observation of cell sheet detachment | Recovery rate (%) | Observation of cell sheet detachment |
| Example 2.1 | >90 | Partly detached | >90 | Overall favorable | >90 | Overall favorable |
| Example 2.2 | >90 | Partly detached | >90 | Overall favorable | >90 | Overall favorable |
| Example 2.3 | >90 | Partly detached | >90 | Overall favorable | >90 | Overall favorable |
| Example 2.4 | >90 | Partly detached | >90 | Overall favorable | >90 | Overall favorable |
| Example 2.5 | 30-80 | Sheet not detached | >90 | Partly detached | >90 | Overall favorable |
| Example 2.6 | >90 | Partly detached | >90 | Overall favorable | >90 | Overall favorable |
| Example 2.7 | >90 | Partly detached | >90 | Overall favorable | >90 | Overall favorable |
| Example 2.8 | >90 | Partly detached | >90 | Overall favorable | >90 | Overall favorable |
| Example 2.9 | >90 | Partly detached | >90 | Partly detached | >90 | Partly detached |
| Example 2.10 | >90 | Partly detached | >90 | Overall favorable | >90 | Overall favorable |
| Example 2.11 | >90 | Partly detached | >90 | Partly detached | >90 | Partly detached |
| Example 2.12A | >90 | Partly detached | >90 | Overall favorable | >90 | Overall favorable |
| Example 2.12B | >90 | Partly detached | >90 | Partly detached | >90 | Overall favorable |
| Example 2.13A | >90 | Partly detached | >90 | Overall favorable | >90 | Overall favorable |
| Example 2.13B | >90 | Partly detached | >90 | Partly detached | >90 | Overall favorable |
| Example 2.14A | >90 | Overall favorable | >90 | Overall favorable | >90 | Overall favorable |
| Example 2.14B | >90 | Partly detached | >90 | Overall favorable | >90 | Overall favorable |
| Example 2.15 | >90 | Partly detached | >90 | Overall favorable | >90 | Overall favorable |
| Comparative Example 2.1 | 30-80 | Sheet not detached | >90 | Overall favorable | >90 | Overall favorable |
| Comparative Example 2.2 | <20 | Sheet not detached | 30-80 | Sheet not detached | 30-80 | Sheet not detached |
| Comparative Example 2.3 | <20 | Sheet not detached | 30-80 | Sheet not detached | 30-80 | Sheet not detached |
| Comparative Example 2.4 | <20 | Sheet not detached | <20 | Sheet not detached | <20 | Sheet not detached |

For all the plasma treated microporous films, the cell culture supports manufactured with a lower radiation dosage showed more favorable functions than when polystyrene was used in terms of cell recovery rates and observations of cell sheet detachment. In addition, microporous polycarbonate showed favorable functions even without plasma treatment.

In relation to the microporous polycarbonate film whose pore size was 5 μm used in Example 2.11, although cell sheet detachment took place from an equivalent confluence state, some cells were entangled in the pores. Therefore, cells were entangled in the pores and cell sheet detachment was delayed under observation. Depending on the state of cells being entangled, the cell sheet remained to be damaged even after being detached, and the entire sheet did not completely Test Example 2.4

In the present test, culture medium permeability of a substrate obtained by binding a temperature responsive polymer to the surface of the microporous films (Examples 2.6 through 2.11) which were processed with plasma treatment used in Test Example 2.3 was examined.

The base film used in Example 2.6 was coated with Coating Composition 7 described in Test Example 2.3. The resulting film was subjected to radiation irradiation at a dose of 15 Mrad in a single shot. The obtained film was washed and dried to give the film. For comparison, a base film on which no coating was performed was prepared. Each of these films was set to an aspiration glass holder whose filter was 47 mm in diameter. The aspiration glass holder was installed on a 1 L filtering flask connected to an aspirator to perform filtration by allowing distilled water at 20° C. and 40° C. to flow alternatively. As a result, as shown in Table 2.4, the base film without coating allowed the penetration of both warm water and cold water, and the film whose surface was modified with the temperature responsive polymer allowed the penetration of warm water but virtually blocked the penetration of cold water. The temperature dependence of water permeability was reversible, and switching of permeability by cold and warm water switching showed reproducibility.

It was confirmed that all the plasma treated microporous films had an ability to allow a culture medium to penetrate at 37° C. as described in Table 2.4.

TABLE 2.4

|  | Amount of cold water penetration for 2 minutes | Amount of warm water penetration for 2 minutes |
| --- | --- | --- |
| Base film | 4.9 mL | 5.0 mL |
| Example 2.6 | 0.3 mL | 5.1 mL |

What is claimed is:

1. A method for manufacturing a cell culture support, comprising:
    coating a surface of a substrate with a composition comprising a monomer and an oligomer or pre-polymer dissolved in an organic solvent,
    wherein said oligomer or pre-polymer is at least larger than or equal to a dimer, and prevents the crystallization and precipitation of said monomer;
    initiating the polymerization of said monomer; and
    forming a continuous polymer film that binds to the surface of said substrate,
    wherein cells can adhere to and proliferate on said polymer film to form a continuous cell layer.

2. The method for manufacturing a cell culture support according to claim 1, wherein a weight ratio of the monomer to the oligomer or pre-polymer is in the range from 500:1 to 1:20.

3. The method for manufacturing a cell culture support according to claim 1, further comprising a drying step,
    wherein said polymer film is dried on the surface of said substrate.

4. The method for manufacturing a cell culture support according to claim 1,
    wherein the substrate comprises at least one material selected from the group consisting of
    polyethylene terephthalate (PET), wherein the surface of said polyethylene terephthalate substrate is treated with an adhesion-improving treatment;
    a synthetic resin, wherein the surface of said synthetic resin substrate is processed by either corona treatment or plasma treatment or coated with an acrylic resin,
    a natural rubber having covalent bonds,
    a synthetic rubber having covalent bonds, and
    a silicon rubber containing polysilicon and microporous polycarbonate.

5. The method for manufacturing a cell culture support according to claim 1, wherein the polymer film is covalently bound to the surface of said substrate.

6. The method for manufacturing a cell culture support according to claim 1, wherein said polymerization is initiated by radiation.

7. The method for manufacturing a cell culture support according to claim 1, wherein said polymer film comprises at least one polymer selected from the group consisting of a temperature-responsive polymer, a pH-responsive polymer and an ion-responsive polymer.

* * * * *

UNITED STATES PATENT AND TRADEMARK OFFICE
CERTIFICATE OF CORRECTION

PATENT NO.         : 8,557,583 B2
APPLICATION NO.    : 12/045847
DATED              : October 15, 2013
INVENTOR(S)        : Masanao Watanabe et al.

It is certified that error appears in the above-identified patent and that said Letters Patent is hereby corrected as shown below:

On the Title Page, Item (73)

The second Assignee's name is currently listed as

Tokyo Woman's Medical University

To be deleted: "Woman's"

To be replaced by: Women's

Signed and Sealed this
Sixth Day of May, 2014

Michelle K. Lee
*Deputy Director of the United States Patent and Trademark Office*